United States Patent [19]
Levitt et al.

[11] Patent Number: 5,629,527
[45] Date of Patent: May 13, 1997

[54] DENTAL HYGIENE SYSTEM

[76] Inventors: Gary H. Levitt, 1585 Sorrento Valley Rd. Ste. 103, San Diego, Calif. 92121; Kaley A. Levitt, 12555 High Bluff Dr. te 380, San Diego, Calif. 92130

[21] Appl. No.: 432,607

[22] Filed: May 1, 1995

[51] Int. Cl.$^6$ .............................. A61L 2/10; A45D 44/18
[52] U.S. Cl. ................ 250/455.11; 132/309; 206/581
[58] Field of Search ...................... 250/455.11; 132/309; 206/581

[56] References Cited

U.S. PATENT DOCUMENTS

| | | | |
|---|---|---|---|
| D. 254,762 | 4/1980 | Lundvik | D4/116 |
| D. 290,312 | 6/1987 | Wang | D4/108 |
| D. 315,988 | 4/1991 | Tanaka | D4/108 |
| 3,782,397 | 1/1974 | McCord | 132/84 A |
| 3,842,851 | 10/1974 | Pipitone | 132/311 |
| 3,861,406 | 1/1975 | Sitt | 132/309 |
| 3,894,550 | 7/1975 | Eaton | 132/309 |
| 4,803,364 | 2/1989 | Ritter | 250/455.11 |
| 4,821,752 | 4/1989 | Widlak | 132/309 |
| 4,887,621 | 12/1989 | Vallieres | 132/309 |
| 5,097,852 | 3/1992 | Wu | 132/309 |
| 5,163,561 | 11/1992 | Fitzgerald | 206/581 |
| 5,228,595 | 7/1993 | Booker | 222/78 |
| 5,230,444 | 7/1993 | Dunbar | 222/181 |
| 5,377,830 | 1/1995 | Jeannet | 206/362.1 |

*Primary Examiner*—Jack I. Berman
*Attorney, Agent, or Firm*—Arthur F. Holz

[57] ABSTRACT

A lockable molded box enclosure is configured to contain and store several types and quantities of instruments commonly used for dental hygiene home use, such as toothbrushes and dental floss. The box includes a lid or door and a latch that must be operated in order to gain access to the instruments contained therein, and the latch is constructed to be operated by inserting an instrument related to the steps involved in dental hygiene. The preferred embodiment discloses a box with a hinged lid and a latch operable by inserting a length of dental floss tautly held and downwardly pressed into a slot formed by the edge of the lid and the edge of the box opening, such that the length of floss will depress a spring-biased locking tab.

20 Claims, 3 Drawing Sheets

DENTAL HYGIENE SYSTEM

FIELD OF THE INVENTION

The invention described herein is placed within the field of oral hygiene devices such as toothbrushes and floss containers, and specifically in the field of combination containers that promote daily practice of dental hygiene by providing convenience and efficiency of use.

BACKGROUND OF THE INVENTION

In the present day, advances in oral hygiene and in particular preventive care of teeth and gums have made daily personal oral care for everyone, adult and children of all ages alike, a matter of necessity and routine. Paradoxically, other increasing demands on each person's time every day and competition for attention among dozens of activities make it more difficult to take the time to engage in the various routines of oral hygiene. In other words, as every dentist has heard repeatedly, many people forget to floss, or even to brush regularly at intervals and after meals. The resulting lack of regular prophylaxis or even occasional lapses in daily oral hygiene routine can and does have disastrous results in the form of tooth and gum disease that could easily have been prevented.

Ideally, flossing should take place with every brushing, and brushing is recommended at least two or three times a day. It is a matter of constant reminders, self-motivation, education and re-education to induce every person to properly care for his or her teeth and gums thoroughly, regularly, and routinely. The within invention seeks to provide a gentle reminder and daily re-education of the importance of complete and regular oral care, and does so in the form of an enforced procedure for accomplishing flossing and brushing at the same scheduled event. A container for implements of dental hygiene provides a systematic approach and sequence for the practice of regular oral care steps, and the systematic approach becomes entrenched in the user's daily routines, will improve preventive practices and therefore overall dental health.

It is therefore a primary object of the within invention to promote oral health in a unique and entertaining way that presents all the instruments of oral hygiene in a convenient and controlled system.

A further object of the invention is to contain all the instruments of oral hygiene in a systematic enclosure that will remind and enforce the user to both brush and floss at the same event.

Another object of the invention is to provide a container for the instruments of oral hygiene that will teach children proper use and sequencing of oral health care steps by included means of entertainment and motivation.

Yet another object of the invention is to provide a visible and aural reminder of the need and timing for oral hygiene practice.

Another object still is to enforce the sequence of accessing floss before accessing the user's toothbrush.

A further object is to provide an oral hygiene implements container that can be used to contain other related implements that the user may wish to associate with the oral hygiene process.

A final object of the invention is to provide an oral hygiene systematic device that is simple, inexpensive and can be used to promote oral hygiene within the entire community by means of promotional distribution and provision for advertising to be placed on the device.

DESCRIPTION OF THE RELATED ART

Many combination devices are revealed in the prior art that attempt to make the practice of oral hygiene more convenient to the user. These consist overwhelmingly, as disclosed and listed in the accompanying Information Disclosure Statement, of toothbrushes that also incorporate a means to hold dental floss, either in a dispenser or held taut in an applicator fork. While these attempts are admirable, their very ubiquity in the patent arts for many decades in slight variations speaks to the failure of the attempts to promote hygienic use on a widespread basis. A combination brush-and-floss-pick may have utility to the frequent traveler, but for home use the standard of practice remains as simple toothbrushes and separate floss containers and applicators. Separating the functions of brushing and flossing almost guarantees that they will not be regularly practiced together, and in view of the relative difficulty of flossing and the personal variation in ability to floss, it is commonly flossing practice that is omitted, to the devastation of gums and teeth that would be prevented otherwise.

It remains, therefore, a pressing unmet need to provide a systematic approach to dental care that will link the practice of flossing and brushing together.

BRIEF SUMMARY OF THE INVENTION

This invention uniquely provides a unified container and integrated functionality that promotes the oral hygiene steps of flossing and brushing as linked practices. An enclosure for storage and presentation of dental implements is provided with containing and dispensing means for both toothbrushes and dental floss or similar implementations such as dental tape in a dispenser. The container is normally in a closed and locked position, and at a scheduled dental hygiene event may be unlocked in a way that promotes sequencing of separate steps of flossing and brushing. A length of floss is accessible and dispensed through the container itself via an access hole, and the length of floss is used as the instrument of unlocking the container to gain access to the user's toothbrush inside. This simple sequencing provides powerful psychological reinforcement and reminder of the importance of flossing and brushing together.

A lock means in the form of a spring-biased latch set deep inside a slot provides the mechanism for a length of floss to be inserted in the slot and activate the lock by maintaining the length of floss in tension between the user's hands—the same configuration that the length of floss is used in the operation of flossing—and may then be pressed down to depress and release the latch. Although the preferred embodiment describes a latch operated by a lengthwise insertion of floss, other latch mechanisms could similarly be related to the flossing withdrawal step, such as a latch lever attached to the floss cutting clip plate or clip tab protrusion, whereby the action of forcibly moving a withdrawn length of floss against a resisting cutting surface would move the latching mechanism. This would maintain the order of hygiene steps by requiring floss to be withdrawn and cut before compartment access to the toothbrushes is enabled.

As a further reminder and educational reinforcement of the dental hygiene event and procedures, a clock may be built into the container device for two purposes: it can activate a timing alarm that will announce that a hygiene event is necessary and it can provide timing indicators for the length of separate operations such as flossing or brushing, both of which should continue for a full minute or more.

As the container may be configured in convenient and decorative sizes and models, it may provide therefore the dental implements and educational functions for an entire family. Further, as the configuration can assume a wide variety of forms and still provide the basic implement containment and access functions, specific storage and display for other implements and elements may also be provided to promote the systematic approach to oral hygiene. For instance, as other combination dental devices have done, provision for a toothpaste or mouthwash dispenser to be used at the same hygiene event could also be included. Further, various decorative forms, especially for children or for interior decorative coordination, could easily be incorporated within the spirit of the invention.

The design and configuration of the preferred embodiment discussed below not only accomplishes the stated functional objectives, but presents the storage and access of the dental implements in an organized, compact space, preventing their scattering within the washroom, or separation of the flossing elements from the toothbrushes, a particular problem when children or a careless husband are present in the household.

Another advantage of keeping the instruments of dental hygiene in a closed container is that the instruments themselves will be shielded from dust and environmental contaminants, and the container may be designed to include further means of protection and cleansing for the instruments. For instance, the container may be made water-tight. For further instance, a sterilization means such as an ultraviolet light may be installed in the container and controllably activated for an interval of time as the instruments are replaced and the container closed, establishing a germ-free environment until the container is opened again.

Finally, the simplicity of the device lends itself also to better of dental hygiene through use as a promotional item to be distributed by dental practitioners with advertising material affixed on the ample exterior surfaces of the device, which would not be possible on such prior art combination devices as toothbrush-and-floss-holder instruments.

DETAILED DESCRIPTION OF THE PREFERRED EMBODIMENT

Figure 1:
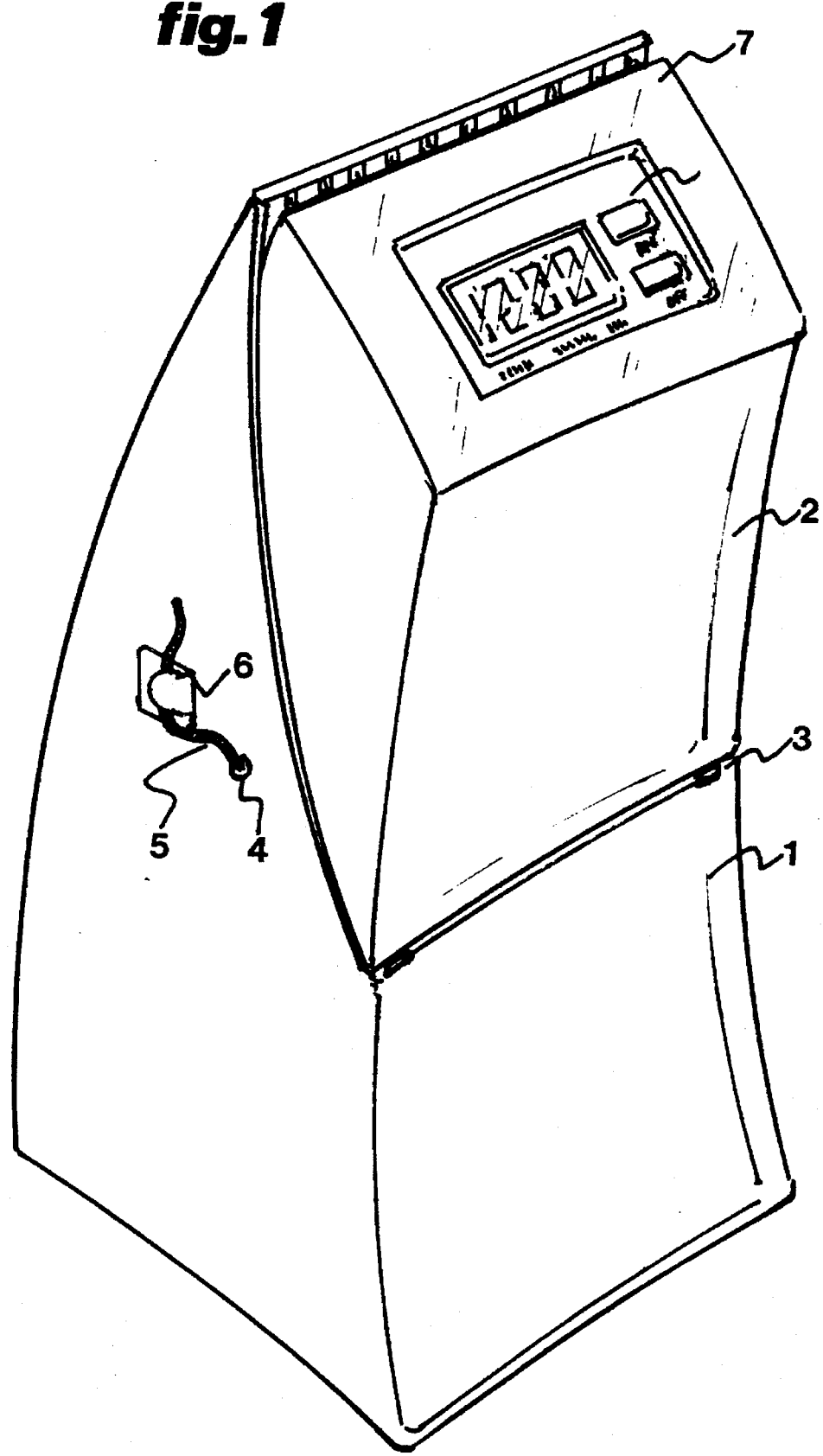
FIG. 1 is a perspective view of the Dental Hygiene System device in closed and locked position.

As illustrated in the appended drawings, the preferred embodiment of the within invention is seen in FIG. 1 as an attractive box container which, as will be seen below provides storage and sequenced access to the implements of dental hygiene contained inside the locked enclosure.

The container form 1 is presented as a simple, generally cubic formed, box with access door 2 supported by hinge 3, which door is shown in closed and locked position and held so by a locking device which is not immediately visible but is accessible as shown later via the lock slot 7 at the junction of the container back and the door top. Note here that within these functional; parameters, the box may be formed in any shape including a variety of other equally functional embodiments; there would be limitless opportunity for cylindrical, spherical or highly irregular external configurations of the container; the preferred embodiment is presented in simplistic form, however, to illustrate not only that even in simple form the systematic presentation will promote the objects and purposes of the invention effectively, but also that the device can be manufactured very inexpensively by reducing desirable but optional decorative, entertaining or amusing design content. The ability to engineer the device for cost reduction and simplicity while retaining all the basic functions and objectives is important since a vital purpose of the invention is to achieve the widest possible promotion of good dental hygiene practices without regard to level of affordability to those most in need of dental disease prevention.

FIG. 1 further illustrates that the dental floss contained inside the device is accessible through floss access hole 4, and a length of floss 5 that may be grasped and pulled to withdraw a further length is shown with its end clipped in floss clip plate 6; the clip tab protrusion that will retain the end of the extended floss also functions as a cutting blade when the floss is pulled sharply downward into the clip, as is typical on many floss dispensers.

Before the functioning of the lock and enforced sequencing of operation is discussed below, note in FIG. 1 that a clock 8 is also provided mounted at the upper surface of door 2. The clock is illustrated as a typical inexpensive digital display with associated controls, and even in a typical inexpensive form would include a user-adjustable aural alarm function that would signal time for the dental care event one or more times per day, and a timing function that may be started and stopped by the control buttons. Thus the device could be presented with a preprogrammed clock timer function set at one minute, and as a user would be visually reminded by placement of the clock to start the timer as flossing or brushing is begun, he would then be reminded to continue the hygiene operation until an alarm sounded at the end of the one-minute interval. Although this timing function is not enforced, the convenience and amusement provided encourages the user to incorporate it into his dental care routine, and especially children will be both taught and entertained by the timing function which tends to hold their attention.

Figure 2:
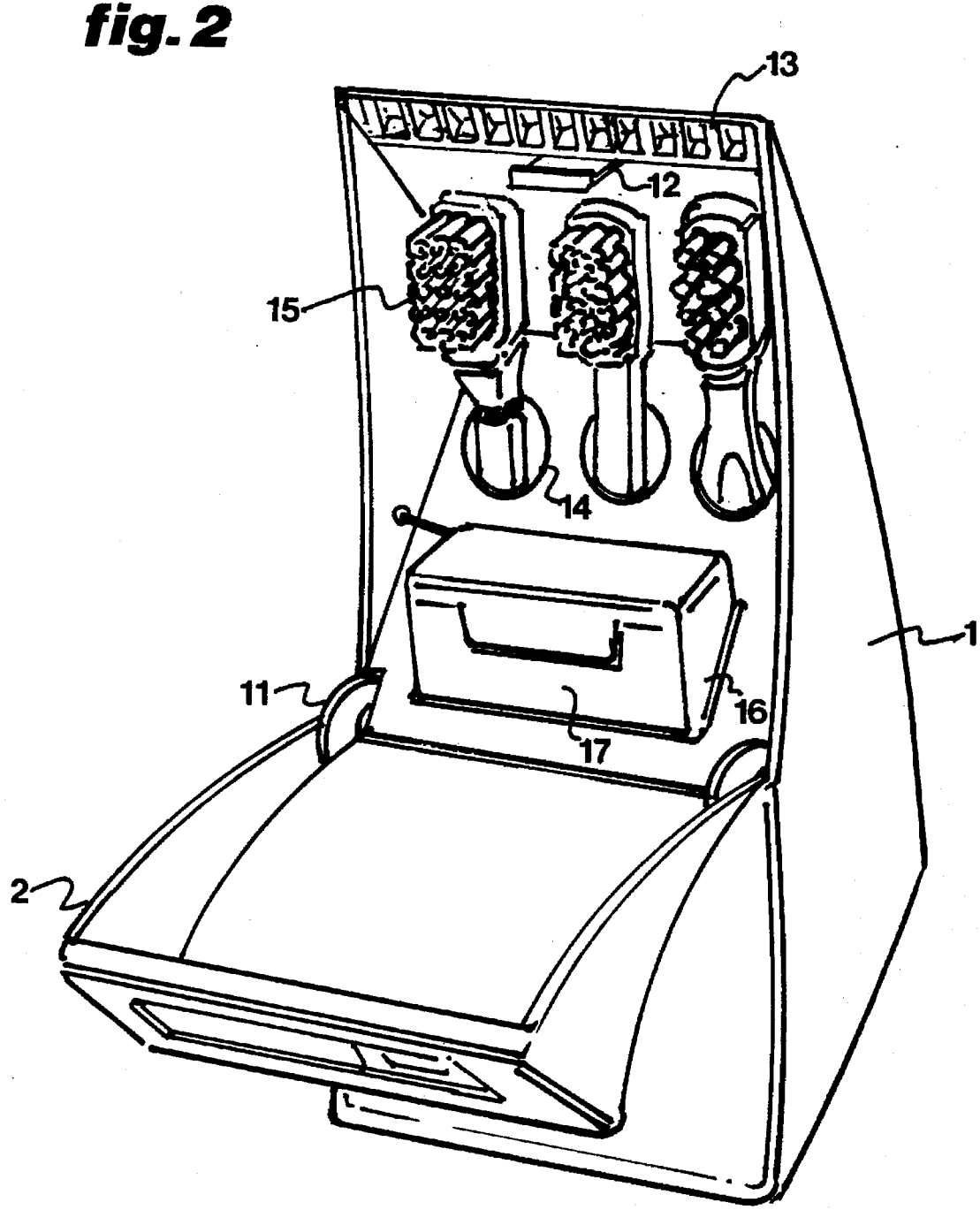
FIG. 2 is a perspective view of the Dental Hygiene System device in open position.

FIG. 2 further illustrates the systematic container device in open position, as door 2 has been unlatched and allowed to drop down, exposing the contents of the container and presenting them to the user's view and access, and supported in this position by door stay brackets 11. Latch 12 may now be seen to be a biased tab 12 protruding othogonally from the container back near but below the top edge 18 of the container back. A lip 19 at the top edge of door 2 provided the latching means that will engage the tab in raised position and latch the container. Bias is provided to the latching tab by construction of semi-flexible material, as the entire container would typically be cast or molded using a plasticized medium, although other materials could clearly be used, such as metallic or combination constructions if the increased cost were justified, as to provide a more decorative model.

Also in FIG. 2 the internal containment of the instruments of dental hygiene may be seen, here shown as a set of 3 toothbrushes 15 of a small family, retained in brush receiving wells 14. Similarly a typical box of commercially available and standard sized dental floss 17 is contained in a closely fitted floss box receiving well 16, which incidentally is positioned such that a length of floss can be extended through and out the floss dispenser hole 4 in the side of the system container.

Figure 3:
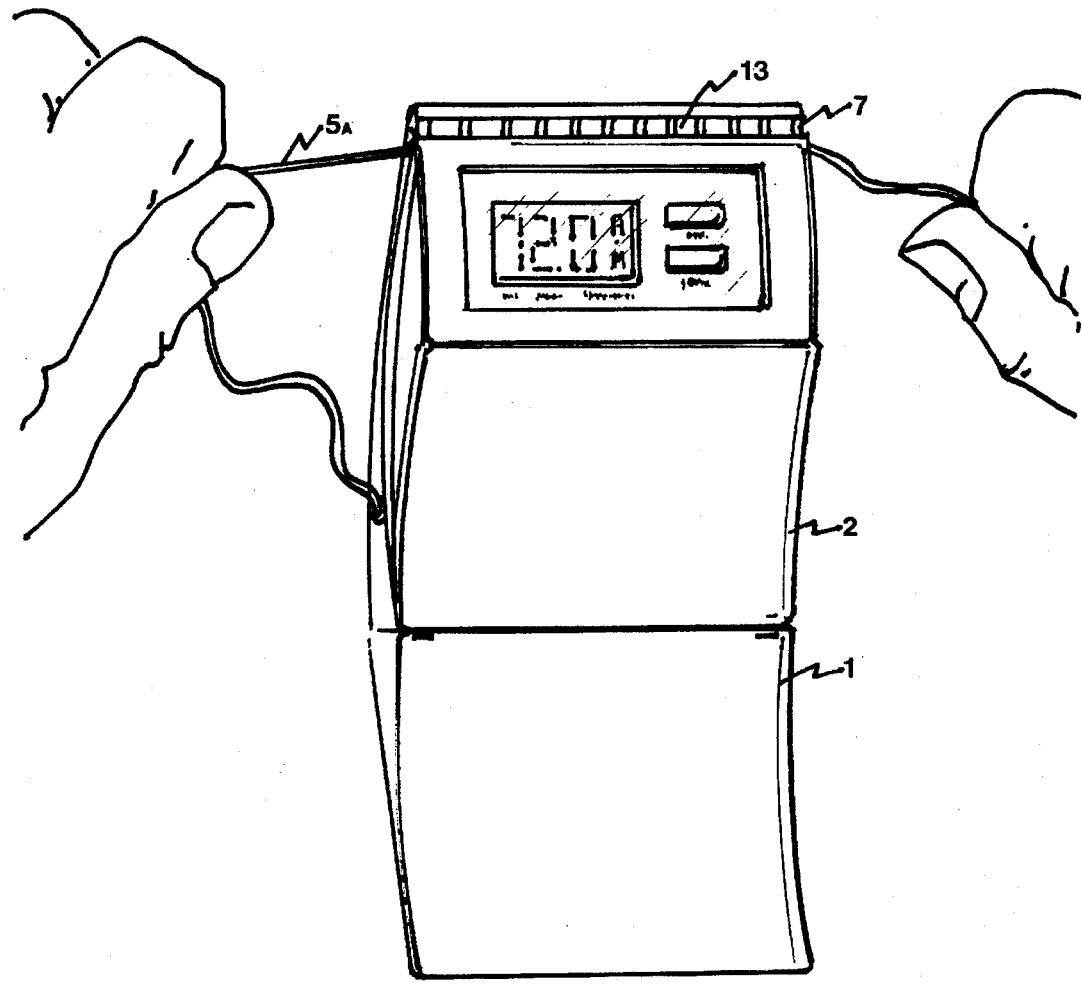
FIG. 3 is a perspective view of the Dental Hygiene System device in use with a user's hands activating the latch mechanism with a length of floss.

FIG. 2 also shows that the top edge 18 of the container back incorporates a series of guide ridges or indentations 13 that serve not only to reinforce and stiffen this component but to define also the distance from the exposed top edge that separates the latching tab 12 from the visible top edge and therefore provides an inset positioning of the latch mechanism in closed mode, the operation of which may be seen in the next drawing, FIG. 3. The spaced ridges further serve to evenly guide and pass the length of floss as it is moved lengthwise into the access gap above the latch.

In FIG. 3, showing once again the dental hygiene system container in closed position, the user's hands are illustrated holding an extended length of dental floss 5A as withdrawn from the floss dispenser hole 4. The floss is held taut by the user, exactly and familiarly as it would be as it is prepared for oral flossing operation, and inserted downwardly into lock slot 7, said slot formed as illustrated before by the conjunction of top edge 18 of the container back and the top edge of door 2, slightly spaced apart by design for insertion of the length of floss. The floss as inserted and held taut is moved downward past guide ridges 13, and will next engage the locking tab as the floss travels downward, providing sufficient but gentle pressure downwardly on the tab to disengage it from the locking lip on the inside of the door and allowing the door to fall forward and down, exposing the interior and contained implements until the door rests on the door stay brackets.

Thus it may be seen that the objectives of the within invention are effectively and conveniently met. The user is forced to withdraw floss to gain access to the toothbrushes contained inside the system enclosure, and only a length of floss can accomplish the purpose, since the slot is too narrow for insertion of fingers or other objects commonly available in the washroom environment. When the floss is extended for unlocking purpose, the user can hardly help be reminded that he should use the floss at that time for its intended prophylactic purpose, either before or after using it in the unlatching operation. The routine of flossing and brushing in a predictable and controlled order, encouraged by the configuration and function of the systematic implement container, is therefore reinforced. When the user is finished with his routine, the implements are conveniently restored to the internal storage wells and the door raised to latch the enclosure, readying it for the next user or event.

In addition to the basic elements and configuration discussed above, it can easily be seen that without changing the functions and attainment of objectives of the invention, other features or configurations could be incorporated. For instance the container could be formed in shapes that would particularly amuse and hold the attention of young children, such as the shape of a friendly dinosaur, configured that its head would form the access door and the hidden floss-activated latching mechanism could be placed in a slot formed by the creature's jaw, reminding the child that he must floss the dinosaur and then floss himself, at which point the dinosaur reminds the child to also brush. In another configuration, the shape of a toy airplane could replace the simple decorative box, and a timer in the form of an egg-timer hourglass could be placed at the airplane propeller position, available to be turned in order to time the one-minute floss and brush intervals.

I claim:

1. A storage container for dental hygiene implements comprising:
    A shaped box having an internal volume shaped to closely contain said implements,
    A door opening in said box and a door fitted to said opening to fully enclose the internal volume,
    And latching means to lockably secure said door to said box, said latching means being operable by one of the contained dental implements.
2. The container of claim 1 wherein said latching means is operable by a string-like length of material.
3. The container of claim 2 wherein said material is dental floss.
4. The container of claim 1 wherein the latching means further comprises a slot formed by the conjunction of one edge of said door and one edge of said opening,
    A biased latch tab within said slot affixed near one said edge,
    Tab-engaging means affixed within said slot near the other edge and engagingly facing said tab.
5. The container of claim 4 wherein said tab further comprises a deformable plastic protrusion.
6. The container of claim 4 wherein said engaging means is a lip on said door transverse to the mating latch tab.
7. The container of claim 1 further comprising a clock with alarm means and setting controls.
8. The container of claim 1 further comprising timer means with setting controls.
9. The container of claim 8 wherein said timer means is a rotatable sand hourglass.
10. The container of claim 1 further comprising one or more molded receptacles shaped for receiving a toothbrush.
11. The container of claim 1 further comprising a molded receptacle shaped for receiving a box of dental floss.
12. The container of claim 1 further comprising an access port through which dental floss stored within said enclosure may be withdrawn.
13. The container of claim 12 further comprising a clip mounted on the exterior of said enclosure configured to retain the end of an extending length of dental floss.
14. The container of claim 13 further comprising a floss cutter.
15. The device of claim 1 further comprising sterilization means within the container.
16. The device of claim 15 wherein the sterilization means is an ultraviolet light and control means to activate said light for an interval sufficient to kill germs within the container.
17. A system for storage and use of dental hygiene implements comprising:
    Lockable means for storage of a plurality of implements including a toothbrush and a dispenser of dental floss and latch means operable by one of said dental implements.
18. The system of claim 17 further comprising a clock mounted to said storage means visible to the exterior when said means is closed.
19. The system of claim 17 further comprising a timer and controls to activate and reset said timer.
20. The system of claim 17 further comprising sterilization means directed toward said implements.

* * * * *